United States Patent [19]

Frischkorn et al.

[11] 4,110,246
[45] Aug. 29, 1978

[54] MIXTURE OF BENZOXAZOLE DERIVATIVES

[75] Inventors: Hans Frischkorn, Hofheim am Taunus; Günter Rösch, Bad Soden am Taunus, both of Fed. Rep. of Germany

[73] Assignee: Hoechst Aktiengesellschaft, Frankfurt am Main, Fed. Rep. of Germany

[21] Appl. No.: 849,090

[22] Filed: Nov. 7, 1977

Related U.S. Application Data

[63] Continuation-in-part of Ser. No. 794,960, May 9, 1977, abandoned.

[30] Foreign Application Priority Data

May 13, 1976 [DE] Fed. Rep. of Germany ....... 2621169

[51] Int. Cl.² .................. C09K 11/06; C07D 263/56
[52] U.S. Cl. ............... 252/301.28; 260/307 D
[58] Field of Search ............... 252/301.28; 260/307 D

[56] References Cited

U.S. PATENT DOCUMENTS

| | | | |
|---|---|---|---|
| 3,314,894 | 4/1967 | Niylas et al. | 252/301.17 |
| 3,336,330 | 8/1967 | Schinzel et al. | 260/307 D |
| 3,767,664 | 10/1973 | Weber | 260/307 D |
| 3,974,172 | 8/1976 | Sahm et al. | 260/307 D |
| 3,993,659 | 11/1976 | Meyer | 260/307 D |

FOREIGN PATENT DOCUMENTS 1,301,791  8/1969  Fed. Rep. of Germany ...... 252/301.28

*Primary Examiner*—F.C. Edmundson
*Attorney, Agent, or Firm*—Connolly and Hutz

[57] ABSTRACT

Compounds of the formula

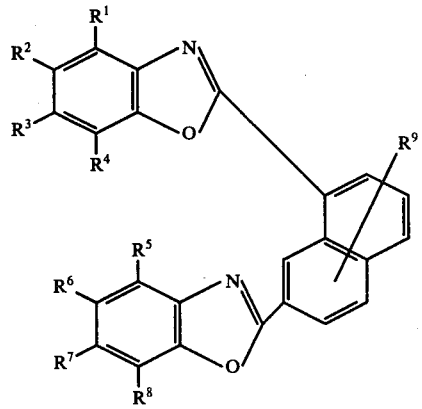

wherein $R^1$ to $R^8$ each mean, independent from one another, a hydrogen atom or a non chromophoric substituent, $R^9$ means a hydrogen atom, an alkyl group, a halogen atom, preferably a chlorine or bromine atom, an optionally functionally modified carboxy or sulfo group. They are prepared by reacting 1 mol of 1,7-naphthalene dicarboxylic acid or its acid chloride with 2 mols of an o-aminophenol and subsequent cyclization of the di-N,N'-acyl compounds obtained in the first step. These compounds are valuable optical brighteners.

6 Claims, No Drawings

MIXTURE OF BENZOXAZOLE DERIVATIVES

This is a continuation-in-part application of application Ser. No. 794,960 filed May 9, 1977, now abandoned.

It is already known to use 1,4-bis-[benzoxazolyl-(2')]-naphthalenes (cf. German Pat. No. 1,282,592, German Offenlegungsschrift No. 1,745,622 and German Offenlegungsschrift No. 2,237,874) and 2,6-bis-[benzoxazolyl-(2')]-naphthalenes (cf. German Pat. No. 1,719,353) as optical brighteners.

The present invention relates to novel 1,7-bis-[benzoxazolyl-(2')]-naphthalenes, which are colorless or slightly yellow, have a pronounced violet to reddish-blue fluorescence in solution and correspond to the formula (1)

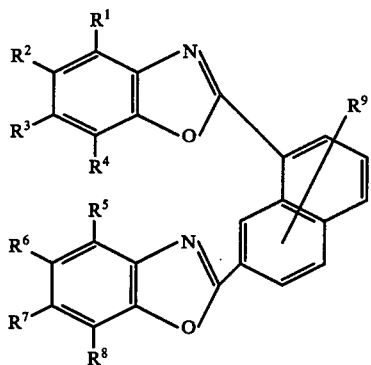

(1)

wherein $R^1$ to $R^8$ each mean, independent from one another, a hydrogen atom or a non chromophoric substituent, $R^9$ means a hydrogen atom, an alkyl group, a halogen atom, preferably a chlorine or a bromine atom, an optionally functionally modified carboxy or sulfo group.

Suitable non chromophoric substituents are in the first place straight chain or branched alkyl groups having up to 18 carbon atoms, preferably up to 12, especially from 1 to 4, which may be substituted by an optionally functionally modified carboxy group, alkenyl groups having preferably from 2 to 4 carbon atoms, aryl radicals, preferably phenyl groups, aralkyl groups, which preferably derive from lower alkylene and phenyl radicals, for example benzyl and phenylethyl groups, acyl, optionally functionally modified carboxy or sulfo groups, arylamino or sulfonyl groups as well as halogen atoms, preferably chlorine atoms. Two lower alkyl radicals may form together a lower alkylene group or a fused benzo ring.

The term "functionally modified carboxy group" generally means to understand carboxylic acid derivatives in the broadest sense, i.e. compounds having one carbon atom, of which three bonds are occupied by hetero atoms, especially oxygen, nitrogen and sulfur. In the narrower sense, this term includes salts with colorless cations, alkali metal or ammonium ions being preferred, and furthermore the cyano group, a carboxylic ester group or a carboxylic acid amide group. Carboxylic acid ester groups especially include those of the formula $COOQ^1$, wherein $Q^1$ means a phenyl radical or an optionally branched lower alkyl group, these substituents containing possibly further substituents, preferably lower dialkylamino, lower trialkylammonium, a hydroxy or a lower alkoxy group. A carboxylic acid amide group is especially a compound of the formula $CONQ^2Q^3$, wherein the substituents $Q^2$ and $Q^3$ each mean hydrogen atoms or lower optionally substituted alkyl groups, which may form together with the nitrogen atom a hydroaromatic ring, moreover acid hydrazides and the analogous thioderivatives.

The term "functionally modified sulfo group" means to understand, in analogous manner to the above statements, radicals, the sulfo group of which is bonded to a hetero atom, i.e. the salts with colorless cations, preferably alkali metal or ammonium ions, and furthermore the sulfonic acid ester groups and the sulfonamide group. The sulfonic acid ester group means to understand especially a compound of the formula $SO_2OQ^1$, wherein $Q^1$ is defined as above, and the sulfonamide group means to understand a group of the formula $SO_2NQ^2Q^3$, wherein $Q^2$ and $Q^3$ are defined as above.

An acyl group means to understand a group of the formula $COQ^4$ wherein $Q^4$ is an optionally substituted, preferably lower alkyl radical or phenyl radical, especially an unsubstituted lower alkanoyl group or the benzoyl group.

The sulfonyl radical means to understand especially a radical of the formula $SO_2Q^4$, wherein $Q^4$ is an optionally substituted lower alkyl or phenyl group, these groups containing possibly as substituents preferably a lower dialkyl amino, a lower trialkylammonium, an acylamino or a sulfo group.

The definitions for the radicals $R^1$ to $R^9$ may quite naturally be combined with one another singly or together in any possible manner without intending the introduction of new matter according to 35 U.S.C. 132 by the formation of such subgroups.

Preferred compounds are those which correspond to the formula (2)

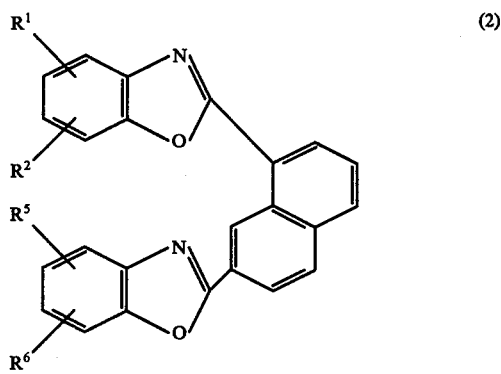

(2)

wherein $R^1$, $R^2$, $R^5$ and $R^6$ are defined as above, $R^1$ being preferably identical with $R^5$ and $R^2$ being identical with $R^6$ and these radicals being preferably in the 5,5'- and 6,6'-position.

Especially preferred are compounds of the formula (3)

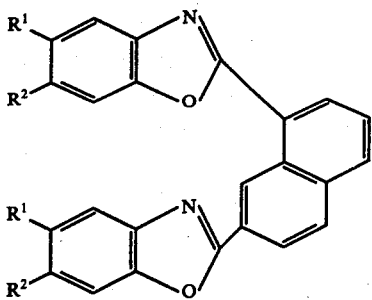

wherein $R^1$ and $R^2$ each mean a hydrogen atom, a $(C_{1-4})$alkyl, a $(C_{1-4})$alkoxy group, a chlorine or bromine atom, a phenyl, carboxy-, carbalkoxy, dimethylaminoalkoxycarbonyl, a hydroxyalkylsulfonyl group or, together a fused benzo ring in the 4,5 or 5,6 position.

The compounds according to the invention can be synthesized in various ways. Two preferred preparation methods are illustrated hereafter.

(a) The dichloride of the naphthalene-dicarboxylic acid-(1,7) is condensed with 2 mols of the o-aminophenols of the formulae (4) or (5)

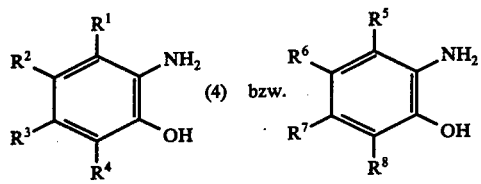

preferably in the presence of an acid acceptor and the bis-acyl-amino-compound obtained of the formula (6)

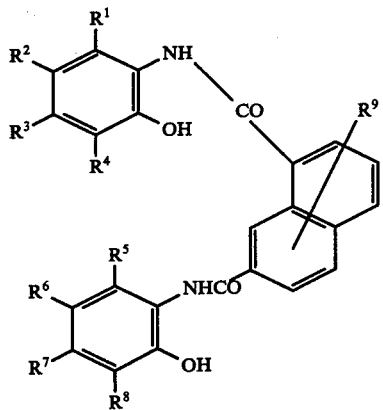

is heated in an inert gas atmosphere, preferably under nitrogen, in high-boiling solvents, preferably in 1,2,4-trichlorobenzene or benzoic acid methyl esters, at inner temperatures of from 180° to 250° C., preferably of from 190° to 220° C., optionally in the presence of catalysts such as zinc chloride or p-toluene-sulfonic acid.

(b) The compounds according to the formula (1) to (3) can principally be synthesized even in a single step process using as starting compounds naphthalene-dicarboxylic acid-(1,7) or a derivative, for example dinitrile and o-aminophenols of the formulae (4) and (5), by heating these components to higher temperatures, suitably of from 150° to 300° C. in an inert gas, preferably under nitrogen. This reaction is preferably carried out in the presence of dehydrating agents. Examples of dehydrating agents or of catalysts acting as dehydrating agents are, boric acid, boric acid anhydride, zinc chloride, aluminum chloride and the polyphosphoric acid, furthermore the pyrophosphoric acid. It may be advantageous to operate with the use of high-boiling solvents, for example dichlorobenzene, trichlorobenzene, α-chloronaphthalene, tetralin or aliphatic, optionally etherified hydroxy compounds, for example ethylene glycol monomethyl ether, diethylene glycol diethyl ether, triethylene glycol dimethyl ether.

The compounds (2) and (3) are obtained by reacting naphthalene-dicarboxylic acid (1,7) with the aminophenols of the formulae (7), (8) or (9)

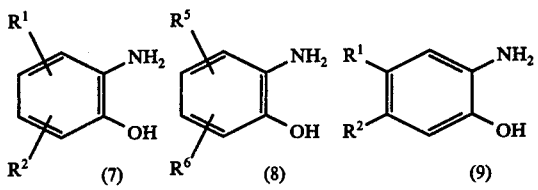

These processes and further processes suitable for the preparation of the compounds of the formulae 1, 2 and 3 are disclosed in the patents and Offenlegungsschriften mentioned in the beginning.

The o-aminophenols of the formulae (4), (5), (7), (8) and (9) are either known in the literature (cf. Beilsteins Handbuch der organischen Chemie, 4th edition, volume XIII) or may by prepared according to methods known to one skilled in the art. The substituents $R^1$ to $R^8$ may also be introduced into the products obtained according to the above mentioned processes by known processes, for example by halogenation, chloromethylation, sulfochloration or by processes starting from chlorosulfonated or carboxy-containing molecules to give compounds having functionally modified sulfo- or carboxy groups or by converting these groups into other groups of this kind or into the free acids, for example by transesterification or hydrolysis.

Suitable o-aminophenols, are, by way of example: o-aminophenol, 3-amino-4-hydroxy-1-methylbenzene, 3-amino-2-hydroxyl-methylbenzene, 4-amino-3-hydroxy-1-methylbenzene, 5-amino-4-hydroxy-1,2-dimethyl-benzene, 5-amino-4-hydroxy-1,3-dimethyl-benzene, 3-amino-4-hydroxy-1-tert.-butylbenzene, 5,6,7,8-tetrahydro-1-amino-2-naphthol, 5,6,7,8-tetrahydro-3-amino-2-naphthol, 5-amino-6-hydroxy-hydrindene, 3-amino-4-hydroxy-diphenyl, 6-chloro-4-amino-3-hydroxy-1-methyl-benzene, 4-chloro-2-aminophenol, 5-chloro-2-aminophenol, 4,6-dichloro-2-aminophenol, and 3-amino-4-hydroxy-1-β-hydroxyethyl-sulfonylbenzene, moreover 2-amino-3-oxybenzoic acid methyl ester, 3-amino-2-oxybenzoic acid methyl ester, 3-amino-4-hydroxybenzoic acid methyl ester or 4-amino-3-hydroxybenzoic acid methyl ester. Instead of methyl esters the following esters of said aminohydroxybenzoic acids may be used: the ethyl, propyl, isopropyl, n-butyl, isobutyl, tert.-butyl, n-amyl, n-hexyl, n-heptyl, n-octyl, n-nonyl, n-decyl, n-undecyl, n-dodecyl and lauryl esters.

Suitable alcoholic compounds for the transesterification are by way of example: tert.-butanol, n-amyl alcohol, 2-ethylbutanol-(1), octanol, cetyl alcohol, lauryl alcohol, cyclohexanol, 2-, 3- and 4-methylcyclohexanol, glycol, propanediol-(1,2), n-butanediols-(1,3) and -(1,4), 2-methyl-n-butanediol-(1,3)-n-hexanediol-(2,5), glycerin, pentaerythritol, diethylene glycol, triethylene glycol, glycol monomethyl ether or monoethyl ether and -mono-n-butyl ether, 3-methoxy-n-butanol-(1), glycide, benzyl alcohol, 2-phenyl-ethanol-(1), 4-isopropylbenzyl alcohol, 2-dimethylaminoethanol-(1), 2-diethylaminoethanol-(1), 2-di-n-butylaminoethanol-(1), 1-dimethylaminopropanol-(2).

The novel compounds according to the invention may be used in a wide field of application owing to their good fluorescent property. Especially those brightening effects may be obtained with them having a somewhat reddish white shade.

Suitable brightening substrates are, by way of example: lacquers, synthetic fibers, for example those consisting of acetyl-cellulose, polyamides, polyolefins, polyvinyl chloride, polyvinylidene chloride, polyacrylonitrile, preferably polyesters, as well as sheets, films, ribbons and shaped articles therefrom.

The compounds insoluble in water may be used as solutions in organic solvents or in aqueous dispersions, preferably with the use of a dispersing agent. Suitable dispersing agents are, by way of example, soaps, polyglycol ethers, which derive from fatty alcohols, fatty amines, or alkyl phenols, cellulose sulfite waste liquors or condensation products of optionally alkylated naphthalene-sulfonic acids with formaldehyde.

The fibrous material is brightened with the aqueous or possibly organic liquor either by an exhaustion processes, at a temperature preferably in the range of from about 20° to 150° C. or under thermosolating conditions, the latter method involving impregnating or spraying the textile material for example with the brightener solution or dispersion and squeezing it off, for example, between rollers to a liquid take-up of from about 50 to about 120%. The textile material is then submitted for a period of from about 10 to 300 seconds to a heat treatment, preferably by dry heat, at a temperature of from about 120° to 240° C.

This thermosolation process can alternatively be combined with further finishing operations, for example finishing with artificial resins in order to impart easy care properties, the materials being optionally condensed after impregnation and drying at 100°-150° C. for a period of from 5 to 20 minutes at a temperature of from 150° to 200° C. for the purpose of cross-linking it.

The compounds according to the invention may also be added to washing detergents. These washing detergents may contain the usual filling agents and auxiliaries, for example alkali metal silicates, alkali metal phosphates or condensed phosphates, alkali metal borates, alkali metal salts of the carboxymethyl-celluloses, foam stabilizers, for example alkanolamides of higher fatty acids or complex forming agents, for example soluble salts of the ethylene-diamine-tetraacetic acid or diethylene-triamine-pentaacetic acid, as well as chemical bleaching agents, for example perborates or percarbonates, perborate activators of the type of polyacetic acid amides, which lead to splitting off of peracetic acid when used with the percompounds, and disinfection agents.

The compounds according to the invention may further by added to high-molecular weight organic materials prior to or during shaping. They may be added, for example, during the preparation of fibers, films, sheets, ribbons, plates or other shaped articles to plastics powders, thermoplastic compositions, melts, polymer solutions or dispersions, for example they may by dissolved in the spinning solutions prior to spinning. Suitable compounds may also be added to the low molecular weight starting materials prior to the polycondensation or polymerization process, for example in the case of polyamide-6, polyamide-6,6 or linear polyesters of the type of polyethylene glycol terephthalates.

It is especially important that the compounds according to the invention, which are substituted by two carboxy or carbalkoxy groups, may be incorporated into linear polyesters and synthetic polyamides by ester or amide bounds, if they are added to these materials or preferably to their starting compounds under suitable conditions. Brighteners which are incorporated into a substrate by a chemical bond in said manner are distinguished by extremely high sublimation and solvent fastness properties.

In the above application field, preferably in the brightening of fibrous material by the exhaustion process or under thermosolation conditions, the compounds according to the invention may be used in admixture with brighteners of other classes of compounds, preferably with brighteners of the formula (5),

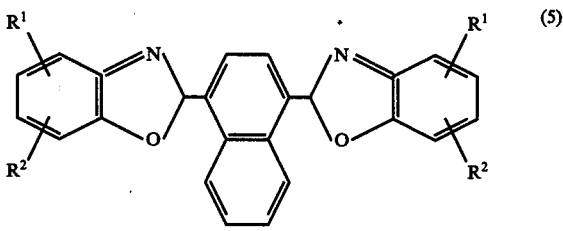

wherein $R^1$ and $R^2$ are defined as above.

A mixture with the compound of the formula (5), wherein $R^1$ and $R^2$ each mean a hydrogen atom, is to be mentioned particularly for textile applications. Thus very good degrees of whiteness reaching from neutral to reddish white shades may be attained.

The shade of the optically brightened substrates may be influenced by varying the ratio of the mixing components, i.e. suitable compounds according to the invention and compounds of the formula (5) and thus the market requirements concerning the nature of the white shades are fulfilled.

Normally 40 to 90% by weight, preferably 50 to 80% of the compound of formula (5) and accordingly 60 to 10% by weight, preferably 20 to 50% of the compound of formula (1) are used. The total amount of the two compounds of formulas I and II taken together, calculated on the material to be brightened, may vary within wide limits, in dependence on the application purpose and on the desired effect. It can be easily determined by simple preliminary tests and is generally in the range of from about 0.01 to about 2%, preferably in the range of from 0.02 to about 0.1%.

The following examples illustrate the invention. The percentages are percentages by weight, unless otherwise stated:

EXAMPLE 1

21.6 parts by weight of naphthalene-dicarboxylic acid-(1,7) and 22.9 parts by weight of o-aminophenol were heated for about 4 hours to about 210° C. (inner temperature) with the addition of 1.5 parts by weight of boric acid in 100 parts by volume of 1,2,4-trichlorobenzene. About 30 parts by volume of trichlorobenzene and water distilled. The reaction mixture was cooled to about 80° to 90° C., about 80 parts by volume of ethanol were added and cooling was continued until room temperature was reached. The precipitated 1,7-bis[benzoazolyl-(2')]-naphthalene (comp. 101) was suction-filtered, washed with ethanol and dried. 30 parts by weight of the above compound were obtained, which had a melting point of from 182° to 183° C. A sample which was recrystallized from toluene melted at a point of from 187° to 188° C. (slightly yellow crystals).

EXAMPLE 2

21.6 parts by weight of naphthalene-dicarboxylic acid-(1,7) and 28.8 parts by weight of 5-amino-4-hydroxy-1,2-xylol were heated while stirring with 150 parts by weight of polyphosphoric acid (85% of $P_2O_5$) to 180° C. within 1 hour and stirred for another 3 hours at 180° C. A homogeneous mass was formed, which was allowed to cool to about 100° C., about 200 parts by volume of hot water (of from 80° to 90° C.) were added dropwise, whereby a precipitate separated. The suspension obtained was further diluted with 500 parts by volume of cold water, cooled to room temperature and the precipitated product was suction-filtered. The resulting product was washed neutral with water and after drying, about 35 parts by weight of 1,7-bis[5,6-dimethyl-benzoxazolyl-(2')]-naphthalene (com. 104) were obtained. A product which was recrystallized from toluene had a melting point from 228° to 230° C. (yellowish crystals).

EXAMPLE 3

21.6 parts by weight of naphthalene-dicarboxylic acid-(1,4) were heated in 100 parts by volume of toluene with 27.8 parts by weight of thionyl chloride for a period of about 3 hours, from an initial temperature of 70° C. to 110° C. Thereafter about 70 parts by volume of solvent were distilled off in a nitrogen current at a temperature of from about 105° to 110° C. and the distilled parts were replaced by fresh toluene. The acid chloride solution thus obtained was added, at a temperature of from 70° to 75° C., within 15 minutes, to a mixture of 33.4 parts by weight of 3-amino-4-hydroxy-benzoic acid methyl ester in 200 parts by volume of toluene, optionally with the addition of 26 parts by weight of dimethylaniline and the resulting mixture was refluxed for 3 hours. Toluene was distilled off by a steam distillation, the aqueous phase was decanted from the precipitated greasy product and the latter was heated with 400 parts by volume of aceton, the turbid solution was clarified and the acylamino compound formed was precipitated by adding 600 parts by volume of water. The resulting mixture was suction-filtered, washed with water and after drying, 44.0 parts by weight of a beige powder were obtained which had a melting point of from 230° to 240° C.

The acylamino compound obtained was cyclized by heating for about 4 hours under nitrogen in 500 parts by volume of benzoic acid methyl ester in the presence of about 2 parts by weight of toluene-sulfonic acid, at a temperature of from about 180° to 190° C. After clarification with about 4 parts by weight of charcoal, about 300 parts by volume of benzoic acid methyl ester were distilled off and after cooling to room temperature, the precipitated 1,7-bis[5'-carbomethoxy-benzoxazolyl-(2')]-naphthalene (comp. 108) was suction-filtered. The resulting product was washed with methanol and after drying there were obtained 32 parts by weight of a yellowish crystalline powder, which could be further purified by recrystallization from benzoic acid methyl ester. Constant melting point of from 259° to 261° C.

EXAMPLE 4

47.8 parts of 1,7-bis[5'-carbomethoxy-benzoxazolyl-(2')]-naphthalene were suspended in 800 parts by volume of isopropanol and 25 parts by weight of potassium hydroxide dissolved in 50 parts by volume of water were added. The reaction mixture was refluxed for 2 hours, 90 parts by volume of water were added and the mixture was refluxed for another 2 hours. The addition of 90 parts by volume of water repeated, and the reaction mixture was kept at the boil for 3 hours. 50 parts by volume of concentrated hydrochloric acid in 300 parts by volume were added, the mixture was digested for about 1 hour at a temperature of from 70° to 80° C., suction-filtered at room temperature, washed neutral with water and dried. Thus 43 parts by weight of a brownish crude product were obtained, which could be further purified by recrystallization from dimethylformamide. The pure 1,7-bis[5'-carboxy-benzoxazolyl-(2')]-naphthalene (comp. 109) melted at a temperature of from 391° to 394° C. and precipitated as light yellow crystals.

EXAMPLE 5

45 parts by weight of 1,7-bis[carboxy-benzoxazolyl-(2')]-naphthalene were heated in 500 parts by volume of o-dichlorobenzene with 50 parts by weight of thionyl chloride for a period of about 5 hours, from an initial temperature of 70° C., up to 100° C. Thereafter about 250 parts by volume of o-dichlorobenzene were distilled off and after cooling, the precipitated acid chloride was suction-filtered and washed with cyclohexane.

The acid chloride which was still moist with the solvent was taken up by 300 parts by volume of dioxane and 15 parts by weight of dimethylaminoethanol were added thereto. The reaction mixture was heated for 2 hours to 80° C., while stirring, diluted with 500 parts by volume of water, clarified with the addition of 5 parts by weight of kieselgur. The pH of the filtered product was adjusted at a value of from 8 to 9 and the reaction product was salted out with sodium chloride. It was suction-filtered and washed with water. After drying, there were obtained 38 parts by weight of a yellowish crude product. By recrystallization from acetic ester pure 1,7-bis[5'-carbo-β-dimethylaminoethoxybenzoxazolyl-(2')]-naphthalene (comp. 110) was obtained as yellowish crystals, which had a melting point of from 115° to 117° C.

The compounds listed in the following table, as far as they have not be mentioned in the Examples 1–5, may be prepared in analogous manner.

TABLE

| No. | R | M.P. | Absorption measured in dimethyl formamide max.[nm] . 10⁻³ |
| --- | --- | --- | --- |
| 101 |  | 187–188 | 342    24,5 |

TABLE-continued

R—[naphthalene]—R

| No. | R | M.P. | Absorption measured in dimethyl formamide max.[nm] | . 10⁻³ |
|---|---|---|---|---|
| 102 | CH₃-[benzoxazolyl] | 189–190 | 354 | 25,2 |
| 103 | [benzoxazolyl]-CH₃ | 168–170 | 355 | 24,9 |
| 104 | CH₃,CH₃-[benzoxazolyl] | 228–230 | 358 | 25,7 |
| 105 | Cl,CH₃-[benzoxazolyl] | 239–241 | 358 | 25,7 |
| 106 | CH₃O-[benzoxazolyl] | 172–175 | 358 | 24,0 |
| 107 | phenyl-[benzoxazolyl] | 182–184 | 357 | 27,2 |
| 108 | CH₃OOC-[benzoxazolyl] | 259–261 | 339 | 25,2 |
| 109 | HOOC-[benzoxazolyl] | 391–394 | — | — |
| 110 | CH₂CH₂OOC-[benzoxazolyl], N(CH₃)₂ | 115–117 | 355 | 25,3 |
| 111 | CH₃OOC-[benzoxazolyl] | 270–272 | 346 | 29,3 |
| 112 | HOCH₂CH₂SO₂-[benzoxazolyl] | 212–222 | 338 | 24,1 |
| 113 | [naphth-benzoxazolyl] | 271–275 | 363 | 27,1 |
| 114 | [naphth-benzoxazolyl] | 271–273 | 354 | 34,0 |

EXAMPLE 6

A fabric of polyethylene terephthalate staple fibers was treated at a goods-to-liquor ratio of 1:20 with a 0.2% aqueous dispersion of the compound 104 which had been prepared with the addition of a dispersing agent (calculated on the weight of the goods), for 1 hour, at 120° C. in a high temperature dyeing apparatus. The sample of the goods had a high degree of whiteness of reddish shade, after rinsing and drying, in comparision with a blank sample.

EXAMPLE 7

A fabric of polyethylene terephthalate staple fibers was treated for 1 hour, at 120° C. in a high temperature dyeing apparatus at a goods-to-liquor-ratio of 1:20 with a 0.08% aqueous dispersion of a mixture consisting of from 50 to 80 parts of 1,4-bis-[benzoxazolyl-(2')]-naphthalene and of from 20 to 50 parts of the compound 102 which had been prepared with the addition of a dispersing agent (1 g/l) calculated on the weight of the goods). The sample had a considerably improved degree of whiteness of neutral to reddish shade, after rinsing and drying, in comparison with unbrightened material.

EXAMPLE 8

A fabric of triacetate was treated for 1 hour at 120° C. in a high temperature dyeing apparatus at a good-to-liquor-ratio of 1:20, under addition of 2 g/l of sodium chlorite and 1 g/l of an activator, with a 0.08% aqueous dispersion of a mixture consisting of from 50 to 80 parts of 1,4-bis-[benzoxazolyl-(2')]-naphthalene and of from 20 to 50 parts of the compound 101. The sample had a very high degree of whiteness, after rinsing and drying, in comparison with a material which had not been brightened.

EXAMPLE 9

A fabric of polyethxlene terephthalene staple fibers was impregnated with a liquor containing 7.5 g/l of a 7% aqueous dispersion of a mixture consisting of from 50 to 80 parts of 1,4-bis-[benzoxazolyl-(2')]-naphthalene and of from 20 to 50 parts of the compound 101. The fabric was squeezed off between two rubber rollers, until the liquor take up had a value of 80% of the weight of the goods. The fabric was then dried on a pin stenter at 190° C. for 45 seconds and fixed. Very good degrees of whiteness of neutral to reddish shade were obtained.

What we claim is:

1. A composition consisting essentially of 60–10% 1,7-bis-benzooxazolyl-naphthalenes and 40–90% of 1,4-bis-benzoxazolyl naphthalenes of the formulas I and II

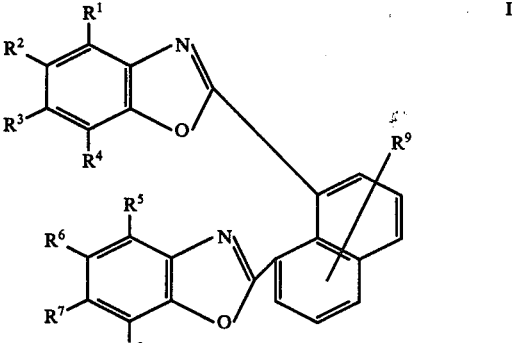

and

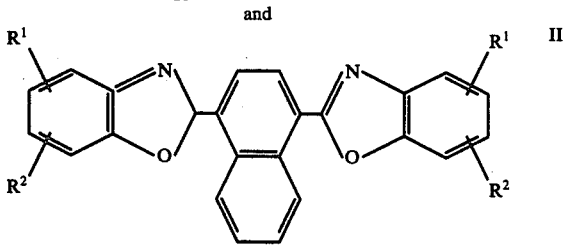

wherein R¹ to R⁸ each are, independent from one another, hydrogen, alkyl of 1 to 18 carbons, C₂–C₄alkenyl, phenyl, C₁–C₄ alkylphenyl, carboxy, —COOR¹⁰, or —SO₂R¹⁰, wherein R¹⁰ is a straight chain or branched alkyl of 1 to 18 carbons, C₁–C₄-hydroxyalkyl, C₁–C₄-alkoxy, C₁–C₄-alkyl, N,N-di-C₁–C₄-alkylamino-C₁–C₄-alkyl or the corresponding quaternary trialkylammoniumalkyl or C₁–C₄-alkylphenyl, or wherein two adjacent groups can form together a C₄-alkylene group or a fused benzo ring and $R^9$ is hydrogen, $C_1$–$C_4$-alkyl, chlorine, cyano or —COOR$^{11}$ or —SO$_2$OR$^{11}$, wherein $R^{11}$ is hydrogen, $C_1$–$C_4$-alkyl, phenyl or $C_1$–$C_4$-alkylphenyl.

2. The composition as claimed in claim 1 wherein the 1,7-bis-benzoxazolyl naphthalene compound is of the formula

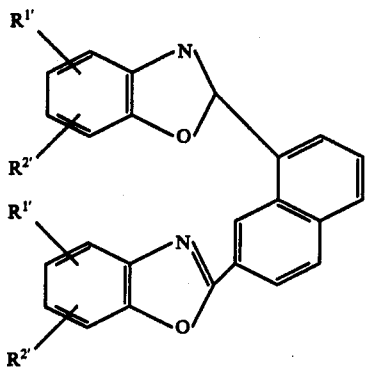

wherein $R^{1'}$ and $R^{2'}$ each are hydrogen or $C_1$–$C_4$-alkyl, $C_1$–$C_4$-alkylphenyl, carboxy, —COOR$^{3'}$ or —SO$_2$R$^{3'}$, wherein $R^{3'}$ is a straight chain or branched $C_1$–$C_4$-alkyl, $C_1$–$C_4$-hydroxyalkyl, $C_1$–$C_4$-alkoxy-$C_1$–$C_4$-alkyl, N,N-di-$C_1$–$C_4$-alkylamino-$C_1$–$C_4$-alkyl or the corresponding quarternary trialkylammoniumalkyl or $C_1$–$C_4$ alkylphenyl, or wherein $R^1$, and $R^2$ are together a $C_4$-alkylene group or a fused benzo ring.

3. The composition as claimed in claim 1 wherein the 1,7-bis-benzooxazolyl naphthalene compound is of the formula

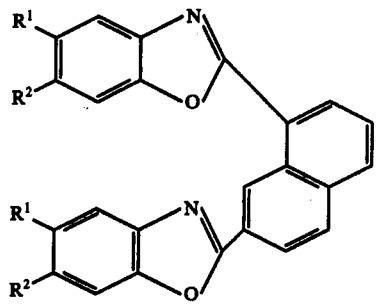

wherein $R^1$ and $R^2$ each are hydrogen, a $(C_1$–$C_4)$alkyl, $(C_1$–$C_4)$ alkoxy, chlorine or bromine, phenyl, carboxy, $C_1$–$C_4$-carboalkoxy, dimethylamino-$C_1$–$C_4$-alkoxycarbonyl, hydroxy-$C_1$–$C_4$-alkylsulfonyl or are together a fused benzo ring in the 4,5- or 5,6-position.

4. The composition as claimed in claim 1 wherein the 1,4-bis-benzooxazolyl naphthalene compound is of the formula

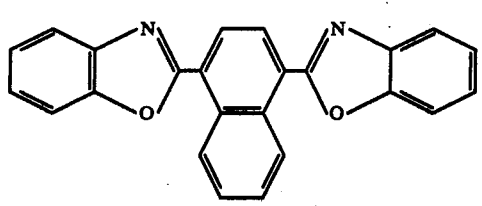

5. The composition as claimed in claim 1 wherein the 1,7-bis-benzoxazolyl-naphthalene compound is a defined in claim 2 and the 1,4-bis-benzoxazolyl-naphthalene compound is as defined in claim 4.

6. The composition as claimed in claim 1 wherein the 1,7-bis-benzoxazolyl-naphthalene compound is as defined in claim 3 and the 1,4-bis-benzoxazolyl-naphthalene compound is as defined in claim 4.

* * * * *